United States Patent [19]

Ranade

[11] Patent Number: 4,792,448
[45] Date of Patent: Dec. 20, 1988

[54] GENERIC ZERO ORDER CONTROLLED DRUG DELIVERY SYSTEM

[75] Inventor: Gautam R. Ranade, East Lyme, Conn.

[73] Assignee: Pfizer Inc., New York, N.Y.

[21] Appl. No.: 61,925

[22] Filed: Jun. 11, 1987

[51] Int. Cl.[4] ............... A23K 1/18; A61K 9/44
[52] U.S. Cl. ..................... 424/438; 424/467
[58] Field of Search ............ 424/438, 468, 467; 604/890, 892; 427/3

[56] References Cited

U.S. PATENT DOCUMENTS 3,851,648 12/1974 Brooke .................... 128/260
4,690,824 9/1987 Powell et al. ............. 424/468

Primary Examiner—Michael Lusignan
Attorney, Agent, or Firm—Peter C. Richardson; J. Trevor Lumb; James M. McManus

[57] ABSTRACT

A device for zero order releasing of biologically active substances into a fluid medium comprising a cylindrical tablet or bolus covered with an impermeable wall or coating from which strips of said wall or coating have been removed.

32 Claims, 7 Drawing Sheets

GENERIC ZERO ORDER CONTROLLED DRUG DELIVERY SYSTEM

BACKGROUND OF THE INVENTION

A readily manufactured device which will dependably release an active material (e.g., a pharmaceutical agent, a cleanser or a deodorizer) at a zero-order rate into a fluid medium (gaseous or liquid) has remained an elusive goal, particularly when the device is in the form of a tablet for controlled in vivo release of a pharmaceutical agent into a biological fluid (e.g., the fluid of the gastrointestinal tract).

An early proposed method was that of Jacobs, U.S. Pat. No. 3,113,076 (1963) in which the drug was combined in a suitable carrier and tablets obtained by an extrusion method. The principle was to form tablets with approximately equal outer and "inner" surfaces, the latter accessed by aperture(s). As the exterior surface is dissolved, the area decreases, while as the inner surface dissolves, the surface area increases. Absent diffusion effects respecting the interior surface, the total surface, and thus rate of solution, would remain relatively constant. In its simplest form, Jacobs' tablet is a cylinder achieving equal inner surface by a multiplicity of cylindrical holes which are parallel to the axis of the outer cylinder, and accessed by the multiple apertures at each end of the cylinder. A related, but more sophisticated device, which now takes into account diffusion effects with respect to the inner surfaces, is that of Brooke, U.S. Pat. No. 3,851,648 (1974). Brooke discloses a cylindrical container, closed at the ends, with a cavity in the shape of a cylinder sector with the aperture in the form of a slot in the outer surface of cylinder (parallel to the axis of the cylinder), said slot at the apex of the cylinder sector cavity. See also Brooke et al., J. Pharm. Sci. 66, pp. 159–162 (1977). In practice, this device produces release rates which are initially high; Lipper et al., J. Pharm. Sci. 66, pp. 163–164 (1977). It is suggested that the device might be implanted into body cavities, but there is no suggestion for use of this device in the form of an ordinary tablet, or for a method of manufacturing such a tablet. Further, the device described by Brooke contains an inner compartment fully or partially filled with active substance leading to the surface of the device through a cavity.

SUMMARY OF THE INVENTION

We have now discovered a device for the controlled release of one or more active substances into a fluid medium at a substantially constant rate (i.e., zero-order) which comprises said substance homogeneously dispersed, with or without inert excipients, and contained substantially in the shape of a cylindrical tablet or bolus by means of an all-covering, essentially impermeable wall or coating except for one or more strips of removed wall or coating from the side of said device.

A preferred feature of said device is a flat cylindrical side and convex top and bottom. Within this preferred embodiment is especially preferred a cylindrical tablet or bolus having more than one strips of wall or coating removed from the side of said tablet or bolus, wherein the width of said strips can be the same or different from each other.

A second preferred feature of said device is that wherein the substance is biologically active. Especially preferred is a substance having germicidal or pharmacological activity or activity in preventing or reducing odors in or emanating from a fluid medium.

Also part of the present invention is a bolus for oral administration into the reticulum or rumen of a ruminant mammal, said bolus being retained in said rumen or reticulum and releasing one or more active substances into the environment of said rumen or reticulum at a substantially constant rate (i.e., zero-order) over a prolonged period of time, which comprises said active substance or substances homogeneously dispersed in a matrix and contained by means of an all-covering, essentially impermeable wall or coating excett for one or more strips of removed wall or coating from the side of said bolus.

Preferred is a bolus containing morantel or a pharmaceutically acceptable salt thereof as the active substance.

An additional aspect of the present invention is a tablet for oral administration to a mammal which releases a pharmaceutically active substance into the fluid of the gastrointestinal tract of said mammal at a substantially constant rate (i.e., zero-order) over an appreciable time interval which comprises said substance homogeneously dispersed, with or without one or more pharmaceutically acceptable excipients and contained by means of an all-covering, essentially impermeable wall or coating except for one or more strips of removed wall or coating from the side of said tablet.

Preferred is a tablet wherein the substance is an antihypertensive agent. Especially preferred within this group are prazosin, nifedipine, trimazosin and doxazosin.

Also preferred is a tablet wherein the substance is an antianxiety agent. Especially preferred within this group is hydroxyzine and sertraline.

Also preferred is a tablet wherein the substance is a bronchodilator. Especially preferred is the bronchodilator pirbuterol.

Also within the preferred embodiment is a tablet werein the substance is a hypoglycemic agent. Especially preferred is glipizide.

Also preferred is a tablet wherein the substance is a cough or cold agent. Especially preferred are brompheniramine dexbrompheniramine and chlorpheniramine maleates, phenylephrine and pseudoephedrine hydrochlorides and cetirizine.

As applied in the present invention, the term "fluid" is intended to encompass either liquid or gaseous, the term "essentially impermeable wall or coating" embraces any material which prevents any substantial movement of the contents or of the surrounding fluid across the wall or coating, and the term "pharmaceutically active substance" is intended to encompass, but is not restricted to analgesics, anorexics, anthelmintics, antibacterials, anticonvulsants, antifungals, antidepressants, antibiotics, antihistamines, antiulcer drugs, antihypertensives, bronchodilators, immunosuppressants, aldose reductase inhibitors, antiinflammatories and blood glucose lowering agents. The "active substances" used individually or in combination in the bolus device of the present invention include anthelmintics, including morantel, pyrantel, oxantel, piperzine, diethylcarbamazine, levamisole, tetramisole, and hygromycin B; antibacterials including sulfa drugs such as sulfadiazine, sulfanilamide, sulfathiazole, sulfamethazine, sulfaguanidine, and sulfapyridine; tetracyclines, such as 5-oxytetracycline, chlorotetracycline, doxycycline and Mannich bases thereof; penicillins such as ampicillin, penicillin G; aminoglycosides such as neomycin, streptomycin, apramycin, bacitracin as its zinc or methyl disalicyclic acid derivitive; macrolides such as erythromycin, oleandomycin and tylosin; antibacterial growth promotants such as avoparicin, polymyxin, lincomycin, bambermycin and efrotomycin; hormonal growth promotants including diethylstilbestrol, zearalanol and melengestrol acetate; antiparasitic agents such as amprolium; nutritional agents such as salts of magnesium, selenium copper and vitamins such as thiamine hydrochloride; molluscicides such as N-tritylmorphine; and bloat prevention agents such as alcohol ethoxylates and poly(oxyethylene)-poly(oxypropylene)-poly(oxyethylene)-polymers, e.g. poloxalene.

BRIEF DESCRIPTION OF THE DRAWINGS

FIG. 4 shows a similar bolus with a hexagon shaped metal core and the location of the strips of coating removed from the side of the bolus.

DETAILED DESCRIPTION OF THE INVENTION

The present invention is readily practiced, offering advantages over other controlled release devices. One important advantage is the nearly constant (zero-order) rate of release of active ingredient over virtually the entire release period.

The outstanding feature of the devices of the present invention is the simplicity with which they can be prepared. When the device is a bolus or an ordinary cylindrical or drum shaped tablet the active ingredient or ingredients are blended with an inert excipients and formed into the appropriate shape using conventional tablet presses or bolus molds.

The use of inert ingredients or excipients aid in tablet or bolus formation and also in controlling the rate of release of the active substance or substances from the appropriate device. An inert ingredient can be of the dissolution type, wherein it is eroding or dissolving at the same time as the active substance, or it can form a matrix which is not soluble, and retains the shape of the device as the active ingredient is released. The excipients include ethylene-vinyl acetate and ethyl cellulose. A portion of the inactive ingredients of the bolus device, in addition to being that described above, can be a metal core, usually steel. This core is employed to insure that the bolus remains in the rumen or reticulum of the animal being treated, and is not prematurely regurgitated. In cases where a metal insert is deemed undesirable, it can be replaced with a ceramic core or some other dense material.

Following the formation of the tablet or bolus, a coating is applied using coating pans or some other available coating technology. A variety of impermeable coating materials can be employed, such as ethylenevinyl acetate.

Figure 1:
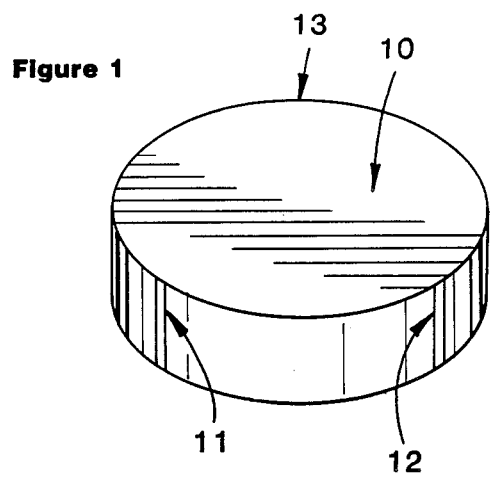
FIG. 1 shows an oblique view of a tablet of the present invention, prepared on a conventional tabletting machine, then coated and uncoated in strips on the side of the tablet.

Once the tablet is coated, a strip or strips are removed from the side. When more than one strip is removed, the removed strips should be placed equidistant from each other around the side of the tablet. Such a tablet is illustrated in FIG. 1, in oblique, having substantially impermeable all-covering wall or coating 10 except for removed wall or coating as strips equidistant from each other 11, 12 and 13.

Figure 2:
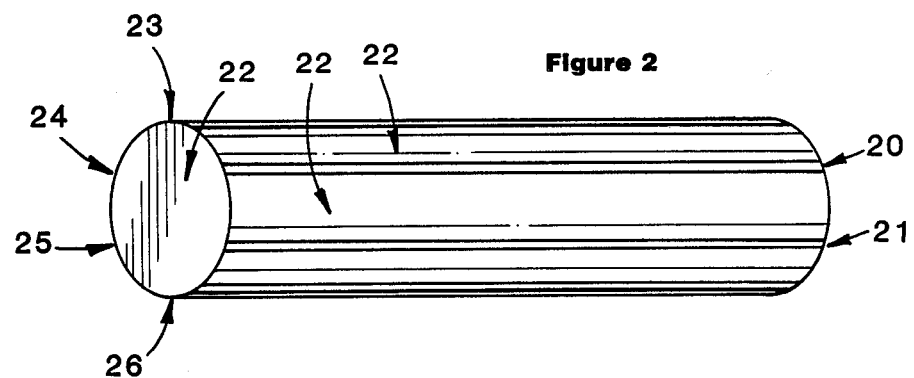
FIG. 2 shows an oblique view of a bolus of the present invention, prepared in a conventional manner, then coated and the coating removed in strips along the side of the bolus.
Figure 3:
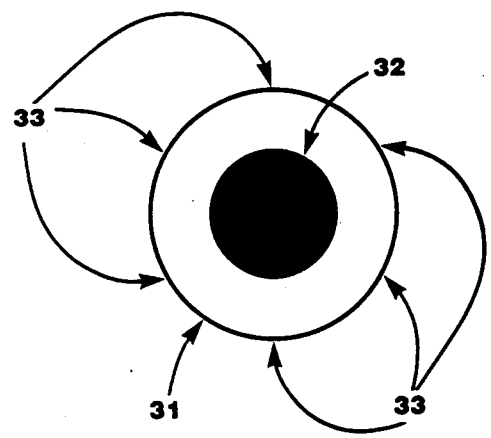
FIGS. 3 and 4 show alternative cross sections of the bolus of FIG. 2. The cross section of FIG. 3 shows the bolus with a cylindrical metal core and the location of the strips of coating removed along the side.
Figure 4:
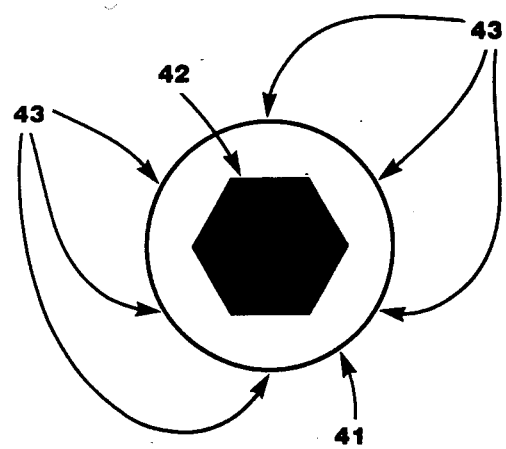

Similarly, a shaped bolus is coated by conventional means as illustrated in FIG. 2, in oblique, the coating 22 then removed in strips 20 and 21 from the side of the bolus. As previously indicated, the strips are spaced equidistant from each other. In order to prevent regurgitation of the bolus device by the animal being treated it is advantageous to use a weighted core in the bolus. This may consist of steel shot or rod running the length of the device. The cross section shape of the rod can be circular as illustrated in FIG. 3, 32 such that the rod is centered in the middle of the device, with the active substance forming a cylindrical shell around the rod. The removed strips of wall or coating 33 are spaced equidistant from each other on the side of the bolus. The shape of the metal insert can vary. FIG. 4 illustrates the cross section of a bolus device in which the hollow cylindrical shell is filled with a rod having a hexagonal cross section 42 shape. In this case the removed strips of wall or coating are placed equidistant from each other and opposite the midpoint of each hexagon side. In a similar manner, a bolus device with four strips removed would accomodate a rod with a square shaped rod, the strips placed equidistant from each other and opposite the midpoint of each side of the square rod side.

Figure 5:
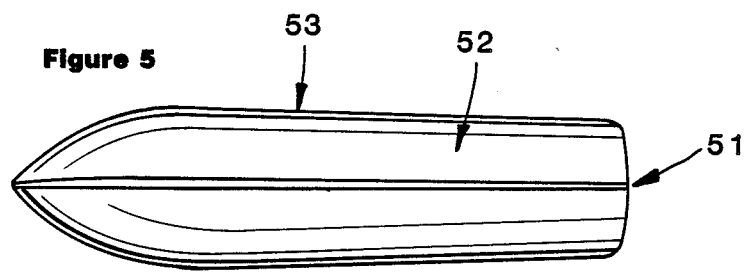
FIG. 5 shows a side view of a device with a different shape which is coated and the coating removed in strips which are equidistant.

The application of the present invention is also meant to apply to cylindrical devices in which the cross section of the bottom of said device is larger than the cross section at the top. An example of such a controlled release device is illustrated in FIG. 5, in side view, 53. Following the conventional formation and coating of such a device the coating 52 is removed as a strip 51 on the side of the device. In this instance, because of the tapering nature of the device, the strip removed is wider at the portion of the device which is wider and tapers to a narrower width at that end of the device which is more narrow. The adjustment of the strip width to the corresponding tapering of the device allows for a prolongation of the zero-order release of the active substance.

Figure 6:
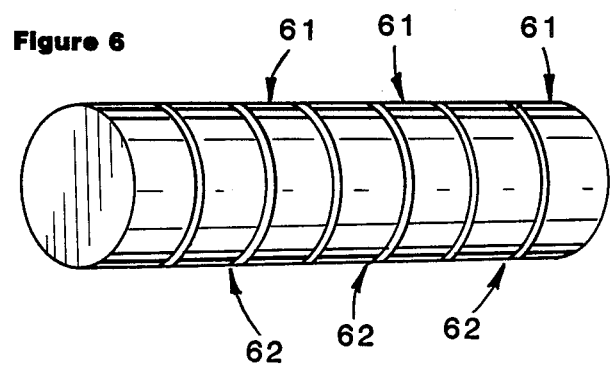
FIG. 6 shows an oblique view of a bolus prepared as that in FIG. 2 in which the coating is removed in strips from the side of said bolus around the circumference of the device at right angles to the longitudinal axis of the device. A heavy insert can be used in the center of the device, if necessary.
Figure 7:
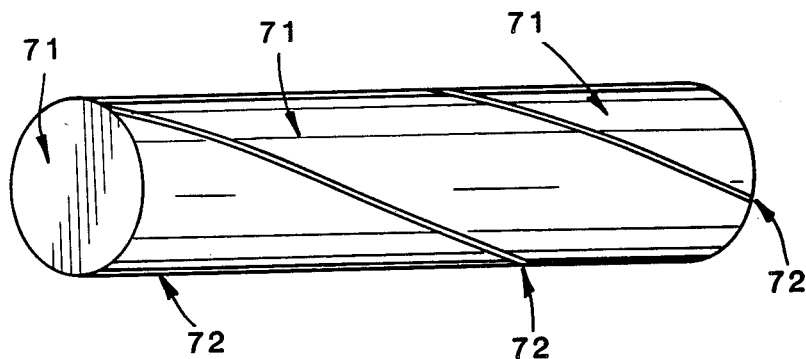
FIG. 7 shows an oblique view of a bolus prepared as that in FIG. 5 in which the coating is removed in strips from the side, at an angle to the longitudinal axis of the bolus.

In addition, to the strip or strips of coating being removed parallel to the longitudinal axis of the device, they can also be removed in other manners and still allow the device to deliver the active substance at a zero-order release rate. FIG. 6 illustrates an oblique view of the bolus similar to that in FIG. 2 with the coating 62 removed in a strip or series of strips 61 circling around the surface at a right angle to the longitudinal axis of the device. If more than one strip is removed the strips should be removed equidistant from one another. Similarly, FIG. 7 illustrates the same bolus in which the coating 72 is removed in strips 71 at an angle to the longitudinal axis of the bolus. Again, if more than one strip is removed they should be placed equidistant from one another.

As previously mentioned, the devices of the present invention can be formed into the various shapes described with excipients, the active compound will generaly be thoroughly blended with conventional, pharmaceutically acceptable excipients to form either devices of the dissolution type (where the excipient disintegrates and generally dissolves along with the active ingredient) or of the matrix type (where the active ingredient diffuses into the surrounding medium leaving the matrix intact). Excipients typically used for either purpose include lactose, sucrose, calcium lactate, magnesium stearate, ethyl cellulose and ethylene vinyl acetate copolymer.

Once formed the tablets or boluses are optionally compression coated (see Ellis et al., Chapter 10, "Tablet Coating", in "The Theory and Practice of Industrial Pharmacy", Lachman et al., eds., Lea and Febiger, 1970, p. 207 et. seq.) to form cylindrical or drum shaped tablets and boluses as illustrated in FIGS. 1-7. The coating materials which are used are substantially impermeable to the device contents and to the ultimate gastrointestinal fluid. A wide range of coating materials can be used and the water flux through the coating can be minimized by the selection of a proper coating thickness. Coating materials which are biodegradable over a longer period can also be employed. On an experimental scale, coating is conveniently accomplished by repeated dipping of the device in a volatile organic solution of a polymer such as ethylene-vinyl acetate copolymer.

The final step in the preparation of the devices of the present invention comprises the removal of the essentially impermeable wall or coating in strips as previously described. Removal of the coating can be by simple manual cutting, but on a commercial scale is carried out by machine cutting, laser cutting or high pressure water cutting.

Figure 11:
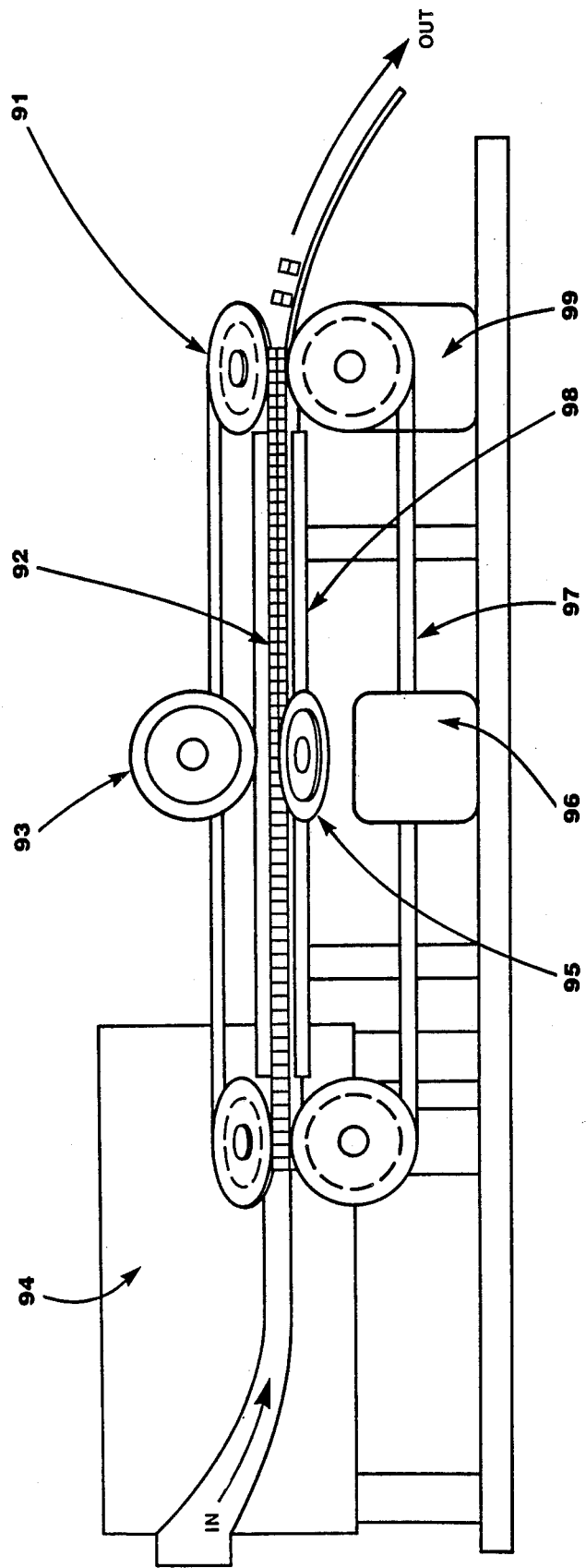
FIGS. 11 and 12 show side and end views, respectively, of a cutting machine used to remove the coating in strips on the aforementioned devices.
Figure 12:
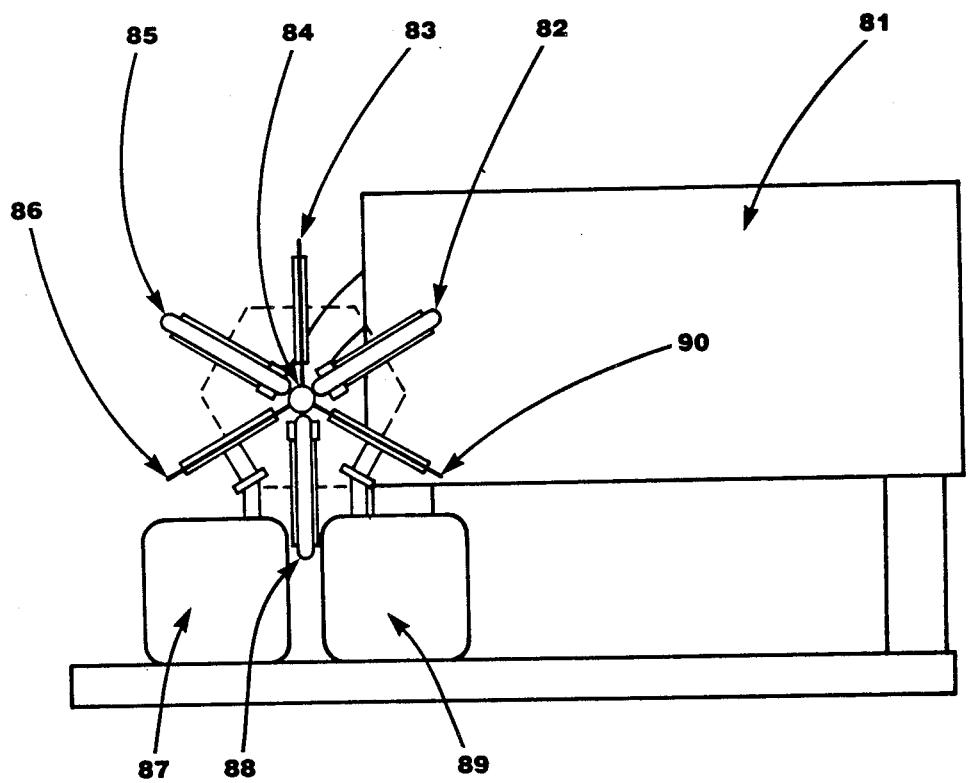

A cutting machine useful for removing strips of coating from the devices of the present invention is shown in FIGS. 11 and 12. In the first figure, a side view of the cutting machine, a vibrating feeder 94 aligns the coated devices 92 as they pass through a portal leading to three drive belts 91 and 97 (shown) driven by drive belt motors 99 (shown) and supported by a drive belt support 98 (shown). As the devices are moved along by the drive belt they encounter three cutters 93 and 95 (shown) driven by cutter motors 96 (shown) the blades of said cutter rotating counter to the direction of the movement of the devices.

The second figure, FIG. 12, shows an end view of the cutting machine showing the vibrating feeder 81, the three drive belts 82, 85 and 88 driven by drive belt motors 87 (shown) and the three cutters 83, 86 and 90 driven by cutter motors 89 (shown). The position of the device 84 as it is positioned in relation to the cutters and drive belts is shown.

This particular cutting machine is set to remove the coating on the sides of the devices at three points equidistant from each other. Similar types of cutting machines can be employed to make more or less cuts to the sides of the devices, as previously mentioned.

The strip or strips of coating which are removed can vary in width. Wider width strips expose more of the active substance to the fluid medium and release the active material more quickly. While the width of the strips can be varied, the release rate from the herein described devices is still zero-order. The ratio of the width of the strip of removed coating or wall to the circumference of the device can be from about 1:16 to about 1:100.

As previously mentioned, if more than one strip of coating is removed they may or may not be of the same width. Further, in the device in FIG. 5, the strip removed can vary in width from top to bottom of side of the device. The uncoated strip dimension can be kept in proportion to the diameter of the device at any point.

The finished devices are tested in vitro for zero order release of the active ingredient as detailed in the Examples below. The in vitro tests are correlated with the in vivo rate of release, for example, by measuring the blood levels of an active agent over time following ingestion of the device.

When the present bolus device is used for delivery of active agent(s) to a ruminant mammal it will generally be in the form of a bolus for long term delivery (.g., 2 weeks or more) in the rumeno-reticular sac (rumen or reticulum) of a ruminant animal, dosed orally by means of a conventional bolling gun. The bolus is designed so that it is of a size that will permit introduction into the rumeno-reticular sac via the esophagus, and retained there by means of its weight, or by means of change in shape which occurs after its administration.

The following examples are given by way of illustration and are not to be construed as limitation to this invention, many variations of which are possible within the scope and spirit thereof.

EXAMPLE 1

Zero-Order Release Tablets-Morantel Tartrate

"A"-Device

A tablet consisting of morantel tartrate and ethylene vinyl acetate copolymer (50:50; w:w) weighing approximately 119 mg was coated with ethylene vinyl acetate by dip-coating the tablet in a 10% solution of ethylene vinyl acetate copolymer in toluene at 55° C. three times, allowing the tablet to dry each time before the next coating. The coating on the side of the tablet, which measured about 0.098" in thickness and 0.334" in diameter, was removed as a strip 0.040" wide and 0.098" long at two positions diametrically opposite each other using a scalpel.

The in vitro release of morantel tartrate from the tablet was determined as a function of time. The test was conducted in water at 40° C. The quantity of morantel tartrate released at a given point in time was determined by direct ultraviolet spectrophotometric assay of a withdrawn sample.

Figure 8:
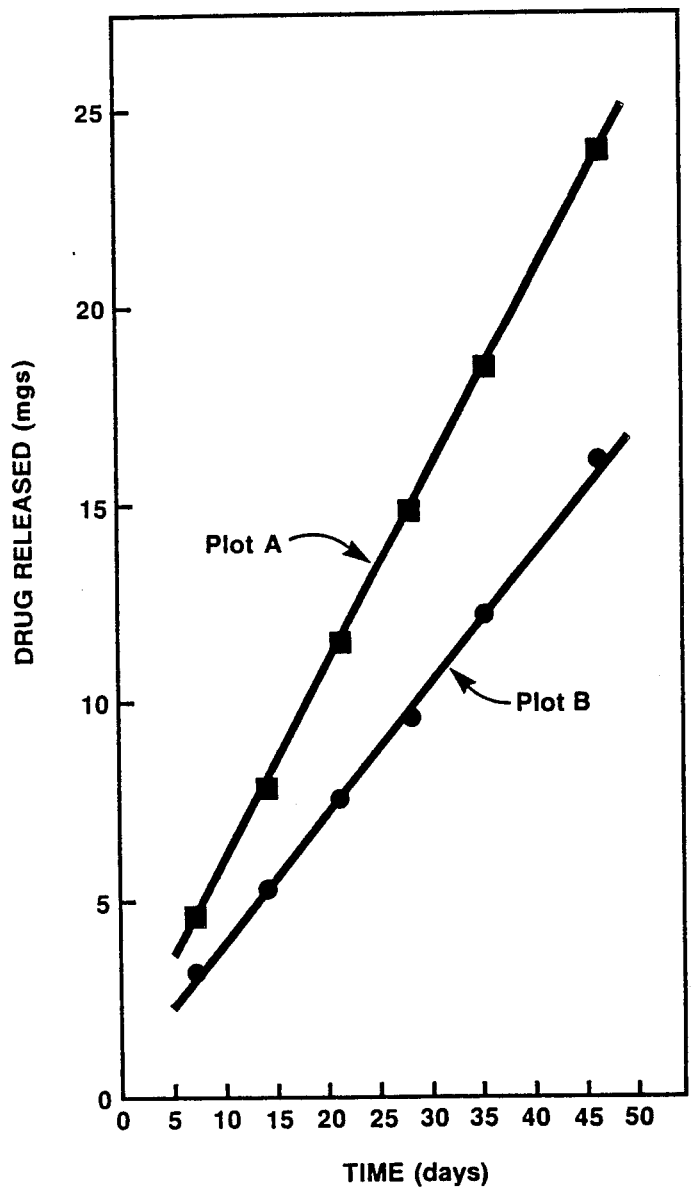
FIGS. 8-10 show the rate of release of active substances from tablets and boluses prepared in the specific examples below.

The results of the test are shown in FIG. 8 as "A" Device.

"B" Device

The above procedure was repeated except that strips of coating were removed at four positions on the side of the tablet. Two measured 0.040" wide by 0.098" long and were made diametrically opposite each other. The second two measured 0.006" wide and 0.098" long and were made diametrically opposite each other and oriented at 90° to the first two removed strips.

The results on the release of morantel tartrate in shown in Figure as "B" Device.

EXAMPLE 2

Zero-Order Release Disk-Morantel Tartrate

Two disks consisting of morantel tartrate and ethylene vinyl acetate copolymer (50:50; w:w) and measuring about 1" in diameter and 0.075" thick were coated as described in Example 1. In the first disk the coating was removed on the side at 5 places equidistant from each other. The width of the strip removed was about 2 mm by the thickness of the disk. The coating of the second disk was removed in a similar manner from six positions equidistant from each other on the side of the disk.

Figure 9:
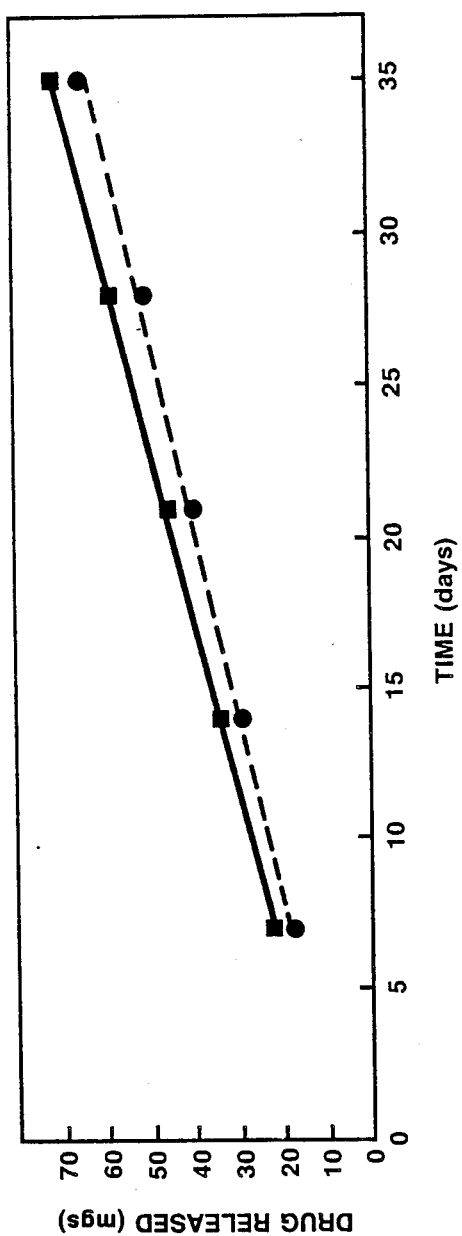

The release of morantel tartrate was measured as described in Example 1 and the results are shown in FIG. 9, the disk having the coating removed from 5 positions being #1 and the disk wherein the coating was removed from six positions being #2.

EXAMPLE 3

Zero-Order Release Bolus-Morantel Tartrate

Five boluses were prepared, using a compression mold with a centered insert in the shape of a hexagon rod approximately 4" in length and a face width of 9/16", containing a 50—50 mixture by weight of morantel tartrate and ethylene vinyl acetate copolymer. The boluses were dip coated using a 10% toluene solution of ethylene vinyl acetate copolymer. The boluses were dipped three times, each time allowing the coating to dry.

Each bolus contained approximately 36.5 g of the 50—50 mixture.

Six strips of coating were removed from each bolus measuring about 0.080" wide and the length of the bolus. The strips were removed opposite the face of the hexagonal insert and spaced equidistant from each other. The ends of the bolus were sealed to prevent loss of the active substance using two coats of ethylene vinyl acetate copolymer.

Figure 10:
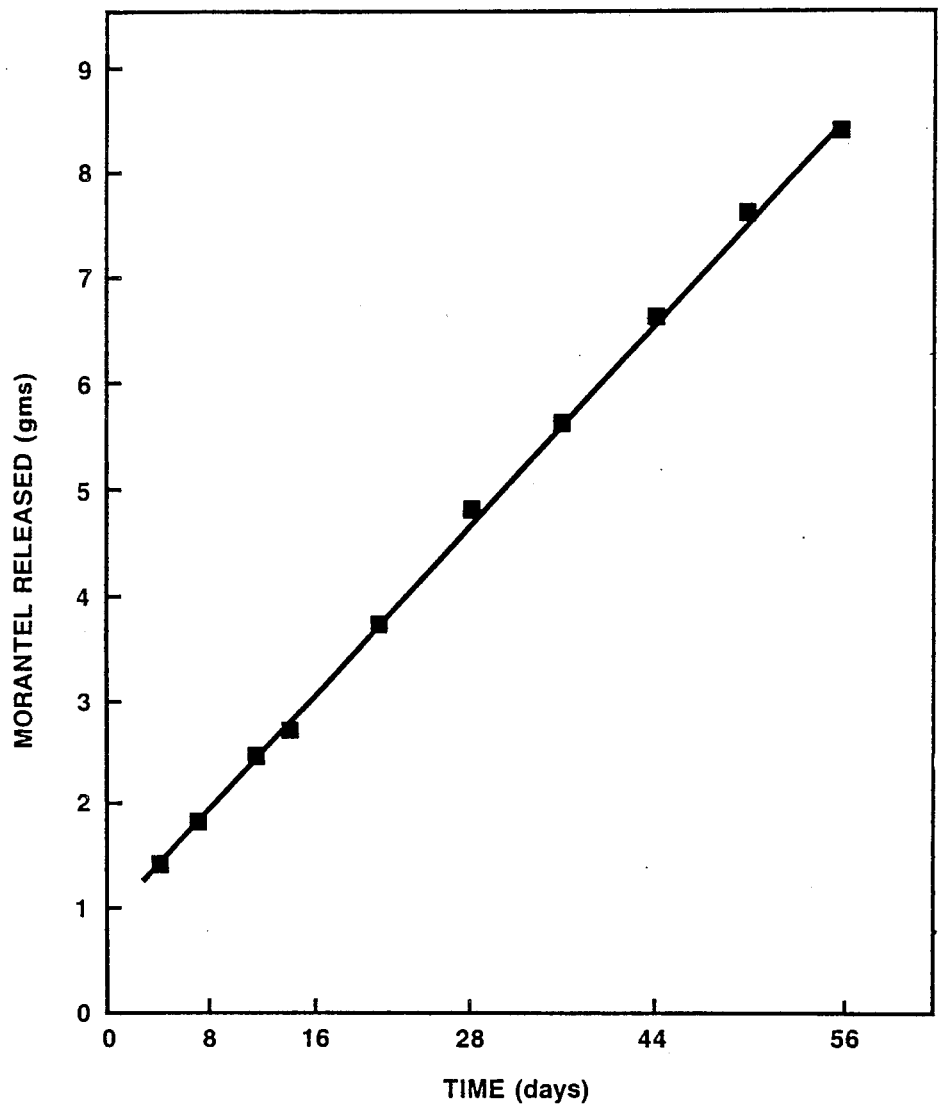

The boluses were then tested as described in Example 1 for the release of morantel tartrate and the results summarized in FIG. 10.

EXAMPLE 4

Zero-Order Release Bolus-Terramycin Hydrochloride

A bolus consisting of a mixture of terramycin hydrochloride and ethylene vinyl acetate copolymer (50—50 by weight) was prepared as in Example 3, with exception that a cylindrical plastic insert was employed in place of the stainless steel.

The formed bolus was coated with ethylene vinyl acetate copolymer using a 10% ethylene vinyl acetate copolymer-toluene solution. The device was dip-coated three times, being allowed to dry each time before the next coating.

The coating was removed at six positions on the side equidistant from each other. Each strip was about 0.080" wide and 4" long, the length of the bolus.

The ends of the bolus were sealed with ethylene vinyl acetate copolymer by dip-coating.

The bolus contained 42.57 g of the mixture of terramycin hydrochloride and copolymer.

EXAMPLE 5

Diaper Pail Deodorant

Following the procedure of Example 1, a large tablet measuring approximately 2.5" in diameter and 1" thick, and comprised of a mixture consisting of p-dichlorobenzene and polyethylene glycol (average molecular weight 1000) in 60:40 portions, is dip-coated with ethylene vinyl acetate copolymer. Strips of the coating measuring about 1/16" wide by 1" long are removed at four positions on the side of the tablet equidistant from one another. The device is used as a deodorant in the air space of a diaper pail, where it is effective for at least several days to several weeks.

EXAMPLE 6

Zero-Order Release Tablet-Sodium Benzoate

A 350 mg tablet consisting of 30% sodium benzoate, 45% ethyl cellulose, 24.5% spray dried lactose and 0.5% magnesium stearate by weight is dip coated with ethylene vinyl acetate copolymer three times, allowing the tablet to dry each time. Three strips of coating measuring about 1 mm wide are removed from the side of the tablet equidistant from one another. When tested according to the procedure described in Example 1, the sodium benzoate is released at a constant rate (zero-order release).

EXAMPLE 7

Toilet Tank Germicide

In a manner similar to Example 1, a tablet measuring 3" in diameter and 1" thick and comprised of O-phenylphenol and p-dioxanone in a weight ratio of 1:10 is dip-coated with ethylene vinyl acetate copolymer and five strips of coating measuring 1/16" wide by 1" long are removed from the side of the tablet equidistant from each other.

The tablet is used in a toilet tank, where it provides effective germicidal action for several weeks under normal use conditions.

I claim:

1. A device for the controlled release of one or more active substances into a fluid medium at a substantially constant rate which comprises said substance homogeneously dispersed, with or without one or more inert excipients, and contained substantially in the shape of a cylindrical tablet or bolus by means of an all-covering essentially impermeable wall or coating except for one or more strips of removed wall or coating from the side of said device.

2. A device of claim 1, wherein the side is flat and the top and bottom are convex.

3. A device of claim 2, wherein more than one strip of wall or coating is removed from the side of said device.

4. A device of claim 3, wherein the width of said removed strips can be the same or different from each other.

5. A device of claim 4, wherein the device is in the shape of a cylindrical tablet.

6. A device of claim 4, wherein the device is in the shape of a bolus.

7. A device of claim 1, wherein the substance is biologically active.

8. A device of claim 7, wherein the activity is to prevent or reduce odors in or emanating from the fluid medium.

9. A device of claim 7, wherein the substance has germicidal activity.

10. A device of claim 7, wherein the substance has pharmacological activity.

11. A bolus for oral administration into the reticulum or rumen of a ruminant mammal, said bolus being retained in said rumen or reticulum and releasing one or more active substances into the environment of said rumen or reticulum at a substantially constant rate over a prolonged period of time, which comprises said active agent or substances homogeneously dispersed in a matrix and contained by means of an all-covering essentially impermeable wall or coating except for one or more strips of removed wall or coating from the side of said bolus.

12. A bolus of claim 11, wherein the active substance is morantel or a pharmaceutically acceptable salt thereof in a polymer matrix.

13. A tablet for oral administration to a mammal which releases a pharmaceutically active substance into the fluid of the gastrointestinal tract of said mammal at a substantially constant rate over an appreciable time interval which comprises said substance homogeneously dispersed, with or without one or more pharmaceutically-acceptable excipients and contained by means of an all-covering impermeable wall or coating except for one or more strips of removed wall or coating from the side of said tablet.

14. A tablet of claim 13, wherein the substance is an antihypertensive.

15. A tablet of claim 14, wherein the substance is prazosin.

16. A tablet of claim 14, wherein the substance is nifedipine.

17. A tablet of claim 14, wherein the substance is trimazosin.

18. A tablet of claim 14, wherein the substance is doxazosin.

19. A tablet of claim 13, wherein the substance is an antianxiety agent.

20. A tablet of claim 19, wherein the substance is hydroxyzine.

21. A tablet of claim 19, wherein the substance is sertraline.

22. A tablet of claim 13, wherein the substance is a bronchodilator.

23. A tablet of claim 22, wherein the substance is pirbuterol.

24. A tablet of claim 13, wherein the substance is a blood-glucose lowering agent.

25. A tablet of claim 24, wherein the substance is glipizide.

26. A tablet of claim 13, wherein the substance is a cough or cold agent.

27. A tablet of claim 26, wherein the substance is brompheniramine maleate.

28. A tablet of claim 26, wherein the substance is chlorpheniramine maleate.

29. A tablet of claim 26, wherein the substance is phenylephrine hydrochloride.

30. A tablet of claim 26, wherein the substance is pseudoephedrine hydrochloride.

31. A tablet of claim 26, wherein the substance is cetirizine.

32. A tablet of claim 26, wherein the substance is dexbrompheniramine maleate.

* * * * *